United States Patent [19]

March

[11] Patent Number: 4,967,738
[45] Date of Patent: Nov. 6, 1990

[54] APPARATUS FOR INDUCING AND MAINTAINING A PENILE ERECTION

[76] Inventor: John P. March, 3759 Erlewine Cir., Sacramento, Calif. 95819

[21] Appl. No.: 421,763

[22] Filed: Oct. 16, 1989

[51] Int. Cl.$^5$ .............................................. A61F 5/41
[52] U.S. Cl. ...................................................... 128/79
[58] Field of Search ................. 128/79; 606/140, 141, 606/157

[56] References Cited

U.S. PATENT DOCUMENTS

| | | | |
|---|---|---|---|
| D. 293,473 | 12/1987 | Chaney | D24/64 |
| 4,539,980 | 9/1985 | Chaney | 128/79 |
| 4,628,915 | 12/1986 | Chaney | 128/79 |
| 4,834,115 | 5/1989 | Stewart | 128/842 |

Primary Examiner—Cary E. Stone
Attorney, Agent, or Firm—Thomas R. Lampe

[57] ABSTRACT

An apparatus for inducing and maintaining a penile erection including a resilient elastic band, handle elements secured at opposed locations on the band, and roller elements disposed between the handle elements to facilitate both placement and removal of the apparatus.

10 Claims, 3 Drawing Sheets

U.S. Patent   Nov. 6, 1990   Sheet 1 of 3   4,967,738
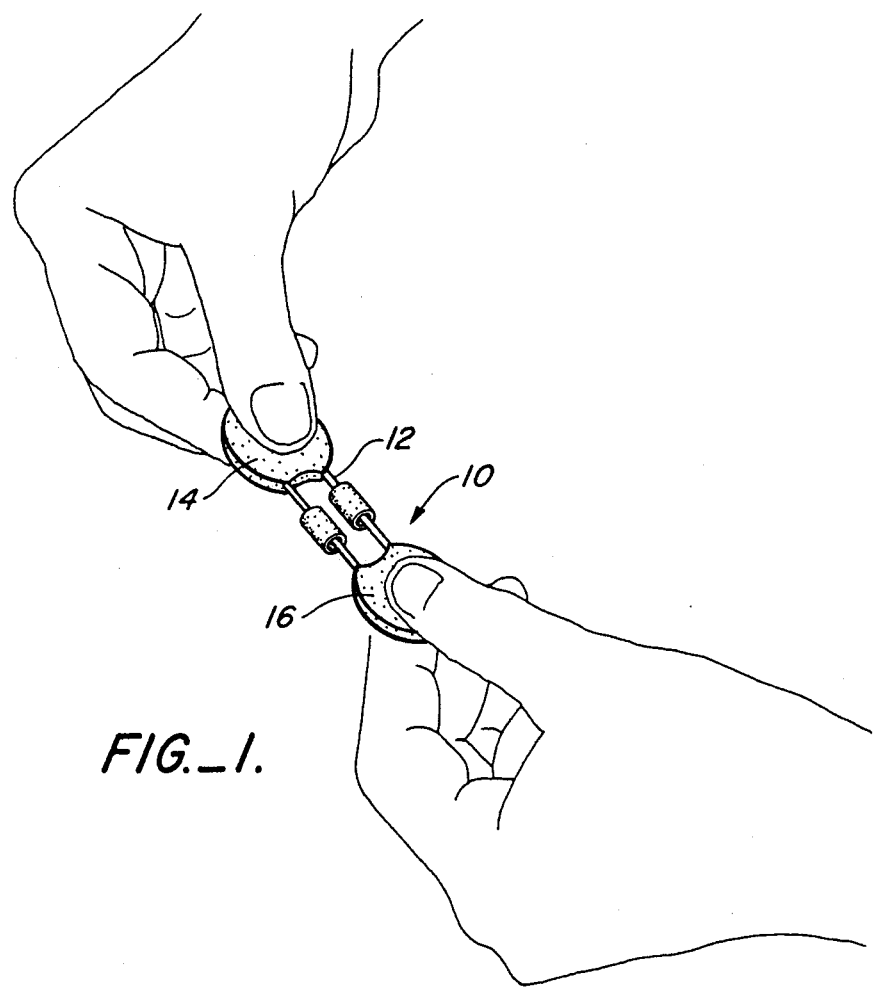
FIG._1.
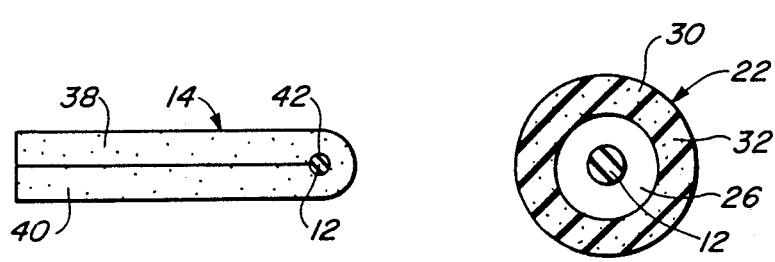
FIG._4.
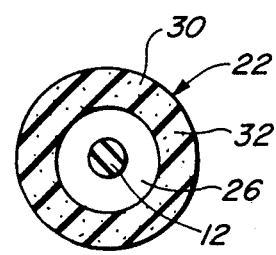
FIG._5.

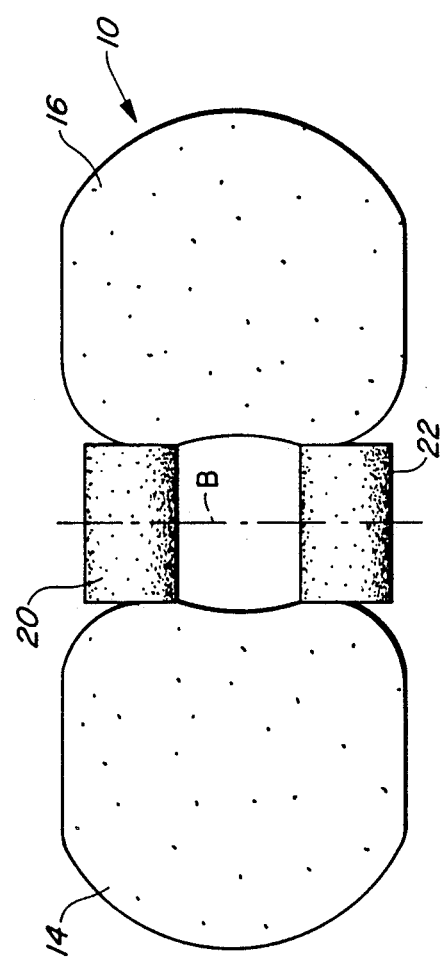
FIG._2.
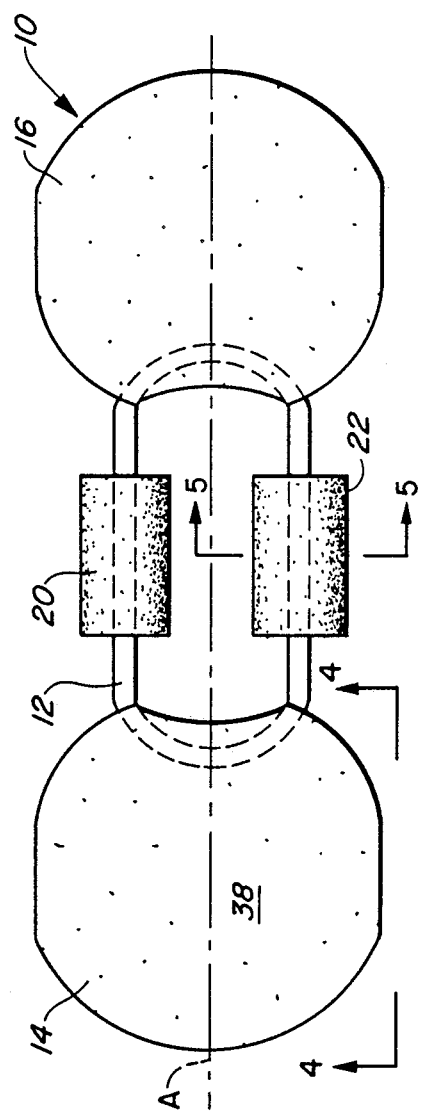
FIG._3.

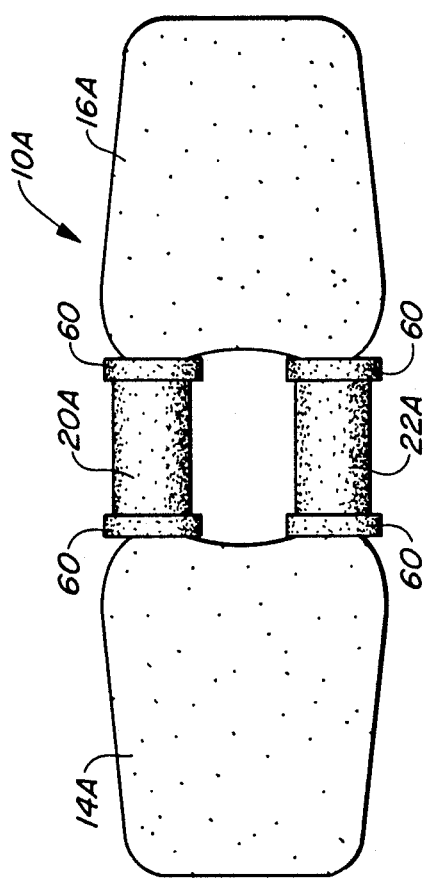
FIG._6.
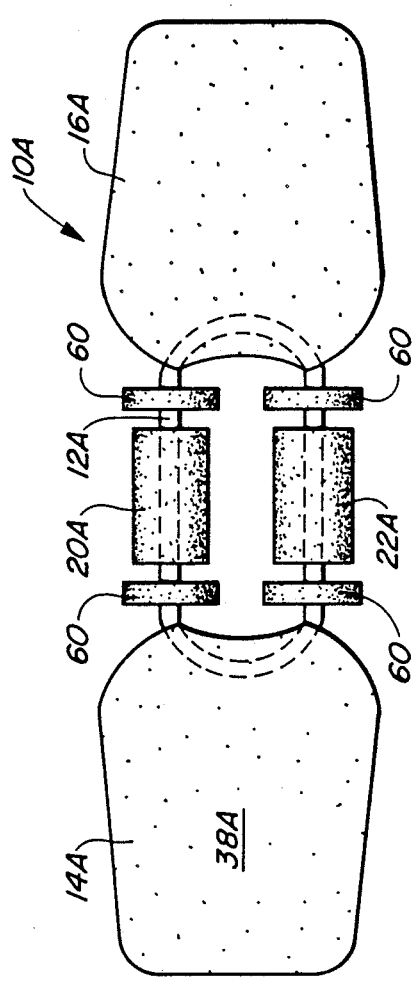
FIG._7.

APPARATUS FOR INDUCING AND MAINTAINING A PENILE ERECTION

TECHNICAL FIELD

The present invention relates to an apparatus for application to a human penis. The apparatus cooperates with the penis to induce and maintain a penile erection.

BACKGROUND ART

A number of arrangements have been devised in the past for solving, or at least attempting to solve, the problem of impotency. Failure to achieve and maintain a penile erection can be caused by many psychological and physical factors. Impotency and the failure to maintain an erection can have a devastating effect on the well-being of not only the afflicted individual but loved ones as well.

The actual physical aspects of penile erection are well understood. Through a mental process, the brain sends messages for blood to flow through an artery at the base of the penis. The pressurized blood fills spongy-tissued chambers located along the penile shaft. Blood flow out of the penis is restricted by small veins along the top of the penis which constrict to trap pressurized blood in the penile chambers.

When the afore-described natural erection process of capturing and holding pressurized blood in the penile chambers is interfered with by failure of the veins at the top of the penis to become or remain constricted, the erection either never takes place or fails prematurely.

A number of approaches have been developed for assisting a male to obtain and maintain a penile erection. One such approach involves the surgical implantation of devices in the penis. Obviously, this is an expensive procedure. Hospitalization is required as are the services of expensive medical professionals. Then, too, surgical implantation techniques can actually cause physical damage to the penis which render it incapable of attaining a natural erection.

A wide variety of devices have been devised over the years which are adapted to be applied to the penis externally and cooperate therewith to promote and maintain an erection. Generally speaking, such devices are characterized by their relative high expense and complexity. Some of these devices are relatively unwieldy, more or less being in the form of external braces. Obviously, devices of this nature can interfere with the act of sexual intercourse.

Devices are known which apply a vacuum to the outside of a penis to enlarge it by inducing blood flow therein. A flexible ring is then attached at the root of the penis to maintain the erection.

A device called a pubis ring has been developed which can be applied externally of the penis for the purpose of maintaining an erection. The pubis ring is intended to be used primarily by males who can develop an erection naturally but cannot maintain it for an extended period of time. The pubis ring comprises a loop with opposed ends which enter opposite ends of a flexible sleeve and emerge together from an aperture in the sleeve. The user reduces the size of the loop by pulling on the ends thereof and securing same. The pubis ring can be difficult to use and the manipulation required to utilize the device can be distracting and detrimental to maintenance of the erection.

U.S. Pat. Nos. 4,539,980, 4,628,915 and Des. 293,473 relate to a system aimed at helping a male obtain and maintain an erection. The system includes an elastic ring centered between two elastic loops attached to the periphery of the ring. The loops are used to stretch the ring radially outwardly to enlarge the opening defined thereby sufficiently to fit over the penis.

The system also includes an accessory which is employed to apply the ring. The accessory includes a cone and integral cylinder positioned on the penis and having the elastic ring stretched thereover. A sleeve is detachably connected to the cone and cylinder and the stretched ring is transferred to the sleeve. The sleeve is then detached from the cone and cylinder and slid down the penis to the root thereof. The ring is then slid off the sleeve at the base of the penis.

The system just described is expensive and employment of a special accessory to facilitate ring placement on the penis is not always convenient or appropriate. Then too, such an accessory is quite bulky as compared to the elastic ring and loop structure itself. It is not always convenient to transport the accessory upon one's person. This means the accessory might not be available when one wishes to employ it.

DISCLOSURE OF INVENTION

The apparatus of the present invention is for application to a human penis and adapted to induce and maintain a penile erection. The apparatus is of inexpensive construction and readily applicable to a penis or removable therefrom without requiring its use in combination with a special accessory.

The apparatus is very comfortable and it may be applied, used and removed with no discomfort whatsoever. The construction of the apparatus renders it capable of multiple reuse. Its simplicity and relatively low expense, however, also mean that, if desired, the apparatus may be employed only once and discarded.

The apparatus of the present invention includes at least one resilient flexible band defining an aperture for receiving a human penis. A first handle element is connected to the band at a first location thereon. A second handle element is connected to the band at a second location on the band. The first and second locations are generally diametrically opposed and disposed along a first axis whereby outwardly directed forces manually applied to the handles will distend the band.

A first roller element is disposed about the band at a third location thereon. A second roller element is disposed about the band at a fourth location upon the band. The third and fourth locations are in generally diametric opposition and disposed along a second axis substantially perpendicular to the first axis.

The roller elements frictionally engage the penis and are rotatable about the band after the penis has been inserted in the aperture of the distended band to facilitate movement of the apparatus to the root of the penis. The band is operable to constrict the penis to restrict blood flow from the penis when the apparatus is disposed at the root and said outwardly directed forces are no longer applied to the handle elements.

The roller elements and the handle elements are formed of soft, resilient, compressible foam material, preferably closed cell polyethylene.

The handle elements and roller elements are each preferably of unitary construction and adapted for ready assembly.

Other features, advantages and objects of the present invention will become apparent with reference to the

BRIEF DESCRIPTION OF DRAWINGS

FIG. 1 is a perspective view illustrating a preferred form of apparatus constructed in accordance with the teachings of the present invention held in the user's hands and prior to application;

FIG. 2 is an enlarged plan view of the apparatus prior to distension of the band thereof;

FIG. 3 is a view similar to FIG. 2 but showing the positions assumed by the apparatus elements when the band is distended;

FIG. 4 is a side view taken in the direction of lines 4—4 of FIG. 3 showing details of a handle element;

FIG. 5 is a cross-sectional view taken along the line 5—5 in FIG. 3;

FIG. 6 is a view similar to FIG. 2 but illustrating an alternative embodiment of the apparatus; and FIG. 7 is a view similar to FIG. 3 of the alternative embodiment.

BEST MODE FOR CARRYING OUT THE INVENTION

Referring now to FIGS. 1-5, apparatus constructed in accordance with the present invention is generally designated by reference numeral 10. The apparatus includes a resilient flexible band 12 defining an aperture for receiving a human penis. A commercially available band of the type commonly known as a rubber band may be utilized. If desired, rather than employing a single band as illustrated in the drawings a plurality of bands may be employed. Whether one or a plurality of bands are employed, the size and strength thereof should be such that they will significantly restrict outflow of blood when applied to a penis. The apparatus may be made available in different sizes to accommodate different sized penises.

Apparatus 10 additionally includes a first handle element 14 and a second handle element 16. The first handle element is connected to band 12 at a first location on the band and the second handle element 16 is connected to band 12 at a second location on the band, said first and second locations being, as shown, generally diametrically opposed and disposed along a first axis A (FIG. 3) whereby outwardly directed forces manually applied to the handle elements will distend the band.

A first roller element 20 is disposed about band 12 at a third location on the band. A second roller element 22 is disposed about the band at a fourth location thereon. The third and fourth locations are in generally diametric opposition and disposed along a second axis B (FIG. 2) substantially perpendicular to the first axis.

The roller elements are formed of a soft, resilient, compressible foam material, preferably closed cell polyethylene foam. Such a material is sold under the name Plastazote by Wilshire Foam Products, Inc. of Carson, Calif. Such material has been found to be ideal for use in the construction of the disclosed apparatus since it is soft, resilient and strong. By utilizing a closed cell construction the roller elements 20, 22 can readily be maintained in a clean condition.

As may perhaps best be seen with reference to FIG. 5, each roller element comprises a strip of soft, resilient, compressible foam material rolled into the shape of a cylinder defining an elongated throughbore 26. Opposed ends 30, 32 of the strip are in engagement and secured together by adhesive. Portions of the band 12 pass through the elongated throughbores of the roller elements and the throughbores are preferably of a somewhat greater diameter than the diameter of the band whereby the roller elements are freely rotatable with respect to the band. This relationship is illustrated in somewhat exaggerated fashion in FIG. 5.

Handle elements 14, 16 are in the form of pads formed of soft, resilient, compressible foam material, preferably the same material utilized in the construction of the roller elements. Each of the handle elements or pads comprises a pair of pad segments 38, 40 integrally connected together along a juncture line 42 and secured together in face-to-face engagement by adhesive. The band 12 is disposed between the pad segments 38, 40 of each pad at the juncture line.

The above-described handle element construction provides maximum structural strength just where it is required when the handle elements are pulled away from one another and the band 12 is stretched as shown in FIGS. 1 and 3. In other words, since the force of the stretched band is applied to each handle element along an integral fold formed therein the band cannot be dislodged from between the pad segments.

It should also be noted that the handle elements are cooperable with the band 12 when outwardly directed forces are applied to the handle elements to stretch the portions of the band passing through the roller element elongated throughbores in a direction generally corresponding to the orientation of said throughbores. This facilitates rotational movement of the roller elements with respect to the band by reducing frictional engagement between the roller elements and band portions. Further reduction in frictional engagement takes place because stretching reduces band diameter.

After the band has been distended by pulling apart the handle elements it may readily be applied to a penis (not shown). The head of the penis is inserted through the aperture formed by band 12. The apparatus is then readily rolled into position to the base or root of the sexual organ. The handles are then released and the band is operable to constrict the penis to restrict blood flow therefrom.

The apparatus of the present invention may be employed to either maintain an existing penile erection or to induce and maintain an erection. The techniques of inducing blood flow into the penis will not be described since they are well known in the art. See, for example, U.S. Pat. No. 4,539,980. It will be appreciated that removal of the apparatus from a penis is also a simple matter, the user simply again pulling the handle elements away from one another and rolling the device off the penis through contact being maintained between the roller elements and the penile shaft.

FIGS. 6 and 7 illustrate an alternative embodiment of the apparatus 10A. This alternative embodiment is essentially the same as that shown in FIGS. 1-5 except that washers 60 formed of soft, resilient, compressible foam material are rotatably disposed on the band 12A at both ends of both roller elements 20A, 22A. It has been found that such an arrangement lessens the possibility of loose skin being pinched by the apparatus during application thereof to a penis.

I claim:

1. Apparatus for application to a human penis and adapted to induce and maintain a penile erection, said apparatus comprising, in combination:

at least one resilient flexible band defining an aperture for receiving a human penis;

a first handle element connected to said band at a first location on said band;

a second handle element connected to said band at a second location on said band, said first and second locations being generally diametrically opposed and disposed along a first axis whereby outwardly directed forces manually applied to said handle elements will distend said band;

a first roller element disposed about said band at a third location on said band;

a second roller element disposed about said band at a fourth location on said band, said third and fourth locations being in generally diametric opposition and disposed along a second axis substantially perpendicular to said first axis, said roller elements frictionally engaging said penis and rotatable about said band after the penis has been inserted in the aperture of the distended band to facilitate movement of said apparatus to the root of the penis, and said band operable to constrict said penis to restrict blood flow from the penis when said apparatus is disposed at said root and said outwardly directed forces are no longer applied to said handle elements.

2. The apparatus according to claim 1 wherein said roller elements are formed of soft, resilient, compressible foam material.

3. The apparatus according to claim 2 wherein said foam material is closed cell polyethylene foam.

4. The apparatus according to claim 2 wherein each said roller element comprises a strip of soft, resilient, compressible foam material rolled into the shape of a cylinder defining an elongated throughbore, said strip having opposed ends secured together, and said band having band portions passing through the elongated throughbores of said roller elements.

5. The apparatus according to claim 4 wherein the opposed ends of each strip are in engagement and secured together by adhesive.

6. The apparatus according to claim 4 wherein said handle elements are cooperable with the band when said outwardly directed forces are applied to the handle elements to stretch said band portions so that said band portions are oriented in a direction generally corresponding to the orientation of the elongated throughbores through which the band portions pass.

7. The apparatus according to claim 1 wherein said handle elements comprise pads formed of soft, resilient, compressible foam material.

8. The apparatus according to claim 7 wherein said foam material is closed cell polyethylene foam.

9. The apparatus according to claim 7 wherein each of said pads comprises a pair of pad segments integrally connected together along a juncture line and secured together in face-to-face engagement, said band being disposed between the pad segments of each pad at said juncture line.

10. The apparatus according to claim 1 wherein washers are rotatably disposed on the band adjacent said roller elements.

* * * * *